(12) United States Patent  
Gabriel et al.

(10) Patent No.: US 8,697,696 B2
(45) Date of Patent: Apr. 15, 2014

(54) TRIAZOLE COMPOUNDS II

(75) Inventors: Stephen Deems Gabriel, Morristown, NJ (US); Andrew Thomas, Binningen (CH)

(73) Assignee: Roche Palo Alto LLC, South San Francisco, CA (US)

( * ) Notice: Subject to any disclaimer, the term of this patent is extended or adjusted under 35 U.S.C. 154(b) by 70 days.

(21) Appl. No.: 13/287,152

(22) Filed: Nov. 2, 2011

(65) Prior Publication Data

US 2012/0115868 A1 May 10, 2012

(30) Foreign Application Priority Data

Nov. 9, 2010 (EP) .................................... 10190548

(51) Int. Cl.
C07D 403/12 (2006.01)
C07D 405/14 (2006.01)
C07D 413/14 (2006.01)
C07D 417/06 (2006.01)
C07D 417/14 (2006.01)

(52) U.S. Cl.
USPC ........ 514/236.2; 514/342; 514/365; 514/380; 514/407; 544/140; 546/269.7; 548/243; 548/255

(58) Field of Classification Search
None
See application file for complete search history.

(56) References Cited

U.S. PATENT DOCUMENTS 8,466,282 B2 * 6/2013 Kuroita et al. ................ 544/130

OTHER PUBLICATIONS

OTANI et al., "Neuroscience Letters" 381:108-113 (2005).
Delong et al., "Autism" 11(2):135-147 (2007).
Solis-Anez et al., "Investigacion Clinica" 48:529-541 (2007).
Papadimitriou et al., "Neuropsychobiology" 43(3):141-144 (2001).
Oyama et al., "Psychobiology" 21:101-105 (1998).
Rueda et al., "Neuroscience Letters" 433:22-27 (2008).
FERNANDEZ et al., "Neuroscience" 10:411-413 (2007).
Cui et al., "Cell" 135:549-560 (2008).
Mckernan et al., "Recombinant Cell Surface Receptors: Focal Point for.:Therapeutic Intervention" (M. J. Browne (Ed.), R. G. Landes Co., Austin, Texas), 8:155-173 (1997).
McCauley et al., "Genetics" 131B:51-59 (2004).

* cited by examiner

Primary Examiner — Kamal Saeed

(57) ABSTRACT

The present invention is concerned with novel triazole compounds of formula (I)

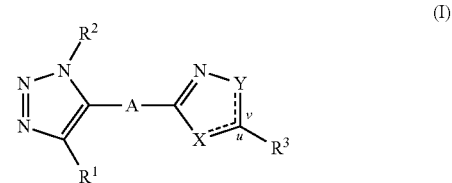

(I)

wherein A, X, Y, u, v, $R^1$, $R^2$, and $R^3$ are as described herein, as well as pharmaceutically acceptable salts thereof. The compounds of present invention have affinity and selectivity for the GABA A α5 receptor. Further the present invention is concerned with the manufacture of the compounds of formula (I), pharmaceutical compositions comprising them and their use as pharmaceuticals.

29 Claims, No Drawings

TRIAZOLE COMPOUNDS II

PRIORITY TO RELATED APPLICATION(S)

This application claims the benefit of European Patent Application No. 10190548.7, filed Nov. 9, 2010, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits. Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I benzodiazepine receptor (BzR) subtypes, whereas α2β2γ2, α3β2γ2 and α5β2γ2 ion channels are termed type-II BzR(R. M. McKernan, P. J. Whiting, in *Recombinant Cell Surface Receptors: Focal Point for Therapeutic Intervention*, M. J. Browne (Ed.) (1997) Chapter 8:155-173, R. G. Landes Co., Austin, Tex.).

It has been shown by McNamara and Skelton (*Psychobiology* (1993) 21:101-108) that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System (*Neuroscience Letts.* (2005) 381: 108-13, *Neuropsychobiology* (2001) 43(3):141-44, *Amer. J. Med. Genetics* (2004) 131B:51-9, *Autism* (2007) 11(2):135-47, *Investigacion Clinica* (2007) 48:529-41, *Nature Neuroscience* (2007) 10:411-13, *Neuroscience Letts.* (2008) 433: 22-7, *Cell* (2008) 135:549-60).

SUMMARY OF THE INVENTION

The present invention provides triazole compounds having affinity and selectivity for the GABA A α5 receptor, their manufacture, pharmaceutical compositions comprising them and their use as pharmaceuticals.

The present invention provides compounds of formula (I)

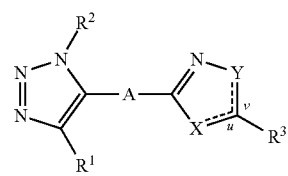

(I)

wherein A, X, Y, u, v, $R^1$, $R^2$ and $R^3$ are as described below and in the claims, and pharmaceutically acceptable salts thereof.

The present invention provides compounds of formula I and their pharmaceutically acceptable salts, preparation of the above mentioned compounds, pharmaceutical compositions containing them and their manufacture as well as use of the above mentioned compounds in the treatment or prevention of diseases related to the GABA A α5. The compounds of present invention are preferably inverse agonists of GABA A α5.

The compounds of present invention and their pharmaceutically acceptable salts have high affinity and selectivity for the GABA A α5 receptor and can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkyl-aryl", "haloalkyl-heteroaryl", "arylalkyl-heterocycloalkyl", or "alkoxy-alkyl". The last member of the combination is a radical which is substituted by the other members of the combination in inverse order.

The term "optional" or "optionally" denotes that a subsequently described event or circumstance may, but need not, occur and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds of formula (I) and stereoisomers, tautomers, solvates, and salts (e.g., pharmaceutically acceptable salts) thereof.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "solvate" denotes crystal forms having either stoichiometric or nonstoichiometric amounts of a solvent incorporated in the crystal lattice. If the incorporated solvent is water, the solvate formed is a hydrate. When the incorporated solvent is alcohol, the solvate formed is an alcoholate.

The term "stereoisomer" denotes a compound that possesses identical molecular connectivity and bond multiplicity, but which differs in the arrangement of its atoms in space.

The term "halo," "halogen," and "halide" are used interchangeably herein and denote fluoro, chloro, bromo, or iodo. A particular halo of the invention is fluoro. A particular example of halo includes fluoro.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. Particular examples of alkyl include methyl and isopropyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by a halogen atom, particularly a fluoro atom. Where more than one hydrogen atom is replaced, the halogen atoms can be the same or different. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common, i.e. the bridge separating the two rings is either a single bond or a chain of one or two carbon atoms. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, bicyclo[2.2.2]octanyl or adamantanyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl include oxetanyl, oxetanyl substituted by one methyl, tetrahydropyranyl and morpholinyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl. Particular examples of aryl include phenyl and phenyl substituted by one fluoro.

The term "aryloxy" denotes a group of the formula —O—R', wherein R' is aryl. An example of aryloxy is phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl, or acridinyl. A particular example of heteroaryl includes pyridinyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

In particular, the present invention provides compounds of formula (I)

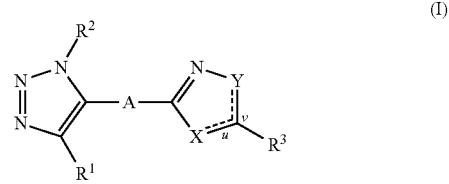

(I)

wherein
A is —CH$_2$—O—, or —CH=CH—;
X is S or CH;
Y is O, NR$^9$ or CR$^9$, with the proviso that if X is S then Y is CR$^9$ and if X is CH then Y is O or NR$^9$;
u and v each independently represent a single bond or a double bond, with the proviso that u and v are not both double bonds and are not both single bonds;
R$^1$ and R$^2$ are each independently alkyl, aryl optionally substituted by 1 or 2 halo or heteroaryl optionally substituted by 1 or 2 halo, wherein one of R$^1$ and R$^2$ is alkyl;
R$^3$ is halo, cyano, alkyl, haloalkyl, nitro, —C(O)R$^4$, or —C(O)NR$^5$R$^6$;
R$^4$ is H, alkyl, aryl, hydroxy, alkoxy or aryloxy;
R$^5$ is H, alkyl, haloalkyl, hydroxyalkyl, —(CH$_2$)$_n$-cycloalkyl, —(CH$_2$)$_n$-heterocycloalkyl, —(CH$_2$)$_n$-aryl, —(CH$_2$)$_n$-heteroaryl, —(CH$_2$)$_m$—NR$^7$R$^8$, or —(CH$_2$)$_m$—OR$^7$, wherein cycloalkyl, heterocycloalkyl, aryl and heteroaryl are optionally substituted by halo, alkyl, haloalkyl, hydroxyalkyl, or alkoxy.
R$^6$ is H, alkyl, or is alkylene together with R$^9$;
or R$^5$ and R$^6$ together with the nitrogen to which they are bound form a heterocycloalkyl;
R$^7$ and R$^8$ are each independently H, alkyl, or aryl;
R$^9$ is H, alkyl, or R$^9$ is alkylene together with R$^6$;
n is an integer from 0 to 6; and
m is an integer from 2 to 6;
and pharmaceutically acceptable salts thereof.

Particular embodiments of present invention are compounds of formula (I) and pharmaceutically acceptable salts thereof.

Further, it is to be understood that every embodiment relating to a specific residue A, X, Y, u, v, R$^1$, R$^2$, R$^3$, R$^4$, R$^5$, R$^6$, R$^7$, R$^8$, or R$^9$ as disclosed herein can be combined with any other embodiment relating to another residue A, X, Y, u, v, R$^1$, R$^2$, R$^3$, R$^4$, R$^5$, R$^6$, R$^7$, R$^8$, or R$^9$ as disclosed herein.

A particular embodiment of the present invention provides compounds of formula (I), wherein
A is —CH$_2$—O—, or —CH=CH—;
X is S or CH;
Y is O, NR$^9$ or CR$^9$, with the proviso that if X is S then Y is CR$^9$ and if X is CH then Y is O or NR$^9$;
u and v each independently represent a single bond or a double bond, with the proviso that u and
v are not both double bonds and are not both single bonds;
R$^1$ and R$^2$ are each independently alkyl, aryl optionally substituted by one halo or heteroaryl,
wherein one of R$^1$ and R$^2$ is alkyl;
R$^3$ is —C(O)NR$^5$R$^6$;

$R^5$ is alkyl, or heterocycloalkyl optionally substituted by alkyl;
$R^6$ is H;
$R^9$ is H or alkyl;
and pharmaceutically acceptable salts thereof.

In a particular embodiment of the invention, A is bound to the triazole ring via a carbon atom.

In a particular embodiment of the invention, A is —CH$_2$—O—.

In a particular embodiment of the invention, A is —CH═CH—.

In a particular embodiment of the invention, X is S and Y is $CR^9$; or X is CH and Y is O; or X is CH and Y is $NR^9$.

In a particular embodiment of the invention, X is S, Y is $CR^9$, u is a single bond and v is a double bond; or X is CH, Y is O, u is a double bond and v is a single bond; or X is CH, Y is $NR^9$, u is a double bond and v is a single bond.

In a particular embodiment of the invention, X and Y together with the carbon and nitrogen atoms to which they are bound form a 5-membered heteroaryl with two heteroatoms, particularly X and Y together with the carbon and nitrogen atoms to which they are bound form a 5-membered heteroaryl selected from thiazol-2-yl, isoxazol-3-yl, and pyrazol-3-yl.

A particular embodiment of the invention provides compounds of formula (Ia)

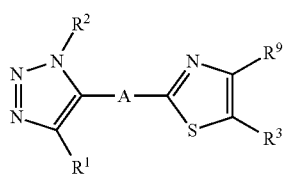

(Ia)

wherein A, $R^1$, $R^2$, $R^3$, and $R^9$ are as defined herein.

A particular embodiment of the invention provides compounds of formula (Ib)

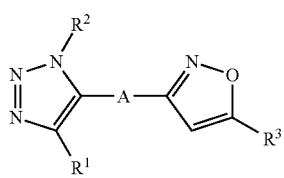

(Ib)

wherein A, $R^1$, $R^2$, and $R^3$ are as defined herein.

A particular embodiment of the invention provides compounds of formula (Ic)

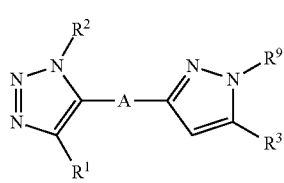

(Ic)

wherein A, $R^1$, $R^2$, $R^3$ and $R^9$ are as defined herein.

A particular embodiment of the invention provides compounds of formula (I')

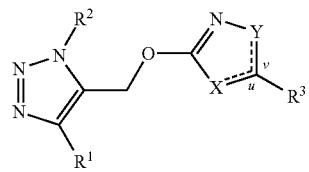

(I')

wherein X, Y, u, v, $R^1$, $R^2$ and $R^3$ are as defined herein.

A particular embodiment of the invention provides compounds of formula (I")

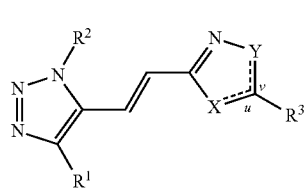

(I")

wherein X, Y, u, v, $R^1$, $R^2$ and $R^3$ are as defined herein.

In a particular embodiment of the invention, one of $R^1$ and $R^2$ is alkyl, and the other one is aryl optionally substituted by one halo or heteroaryl optionally substituted by one halo.

In a particular embodiment of the invention, one of $R^1$ and $R^2$ is methyl, ethyl or butyl, and the other one is phenyl optionally substituted by one halo, or pyridinyl optionally substituted by one halo.

In a particular embodiment of the invention, one of $R^1$ and $R^2$ is methyl, and the other one is phenyl substituted by one fluoro, or pyridinyl.

In a particular embodiment of the invention, $R^1$ is alkyl; and $R^2$ is aryl, or aryl substituted by one halo.

In a particular embodiment of the invention, $R^1$ is methyl, and $R^2$ is phenyl substituted by one fluoro.

In a particular embodiment of the invention, $R^2$ is alkyl; and $R^1$ is aryl, aryl substituted by one halo, heteroaryl, or heteroaryl substituted by one halo.

In a particular embodiment of the invention, $R^2$ is methyl, and $R^1$ is phenyl substituted by one fluoro, or pyridinyl.

In a particular embodiment of the invention, $R^3$ is —C(O)NR$^5$R$^6$.

In a particular embodiment of the invention, $R^5$ is alkyl, or heterocycloalkyl optionally substituted by alkyl.

In a particular embodiment of the invention, $R^5$ is isopropyl, oxetanyl substituted by methyl, tetrahydro-pyranyl, or morpholinyl.

In a particular embodiment of the invention, $R^6$ is H.

In a particular embodiment of the invention, $R^9$ is H or alkyl.

In a particular embodiment of the invention, $R^9$ is H or methyl.

A particular embodiment of the present invention provides compounds of formula (I) as described in the examples as individual compounds as well as pharmaceutically acceptable salts thereof. Furthermore, the substituents as found in the specific examples described below, individually constitute separate particular embodiments of the present invention.

Particular compounds of formula (I) of present invention are those selected from the group consisting of:

3-[5-(4-Fluoro-phenyl)-3-methyl-3H-[1,2,3]triazol-4-yl-methoxy]-isoxazole-5-carboxylic acid (tetrahydro-pyran-4-yl)-amide;
5-[5-(4-Fluoro-phenyl)-3-methyl-3H-[1,2,3]triazol-4-yl-methoxy]-2-methyl-2H-pyrazole-3-carboxylic acid (tetrahydro-pyran-4-yl)-amide;
5-[3-(4-Fluoro-phenyl)-5-methyl-3H-[1,2,3]triazol-4-yl-methoxy]-2-methyl-2H-pyrazole-3-carboxylic acid (tetrahydro-pyran-4-yl)-amide;
5-[3-(4-Fluoro-phenyl)-5-methyl-3H-[1,2,3]triazol-4-yl-methoxy]-2-methyl-2H-pyrazole-3-carboxylic acid morpholin-4-ylamide;
5-[3-(4-Fluoro-phenyl)-5-methyl-3H-[1,2,3]triazol-4-yl-methoxy]-2-methyl-2H-pyrazole-3-carboxylic acid (3-methyl-oxetan-3-yl)-amide;
2-{(E)-2-[5-(4-Fluoro-phenyl)-3-methyl-3H-[1,2,3]triazol-4-yl]-vinyl}-4-methyl-thiazole-5-carboxylic acid isopropylamide;
2-{(E)-2-[5-(4-Fluoro-phenyl)-3-methyl-3H-[1,2,3]triazol-4-yl]-vinyl}-4-methyl-thiazole-5-carboxylic acid (tetrahydro-pyran-4-yl)-amide;
2-{(E)-2-[3-(4-Fluoro-phenyl)-5-methyl-3H-[1,2,3]triazol-4-yl]-vinyl}-4-methyl-thiazole-5-carboxylic acid (tetrahydro-pyran-4-yl)-amide;
2-{(E)-2-[3-(4-Fluoro-phenyl)-5-methyl-3H-[1,2,3]triazol-4-yl]-vinyl}-4-methyl-thiazole-5-carboxylic acid isopropylamide;
4-Methyl-2-[(E)-2-(3-methyl-5-pyridin-2-yl-3H-[1,2,3]triazol-4-yl)-vinyl]-thiazole-5-carboxylic acid isopropylamide; and
4-Methyl-2-[(E)-2-(3-methyl-5-pyridin-2-yl-3H-[1,2,3]triazol-4-yl)-vinyl]-thiazole-5-carboxylic acid (tetrahydro-pyran-4-yl)-amide; and
pharmaceutically acceptable salts thereof.

The invention further provides a process for the preparation of compounds of formula (I) as defined above, comprising:
a) the reaction of a compound of formula (II) with a compound of formula (III) to give a compound of formula (I') wherein A is —CH$_2$—O—

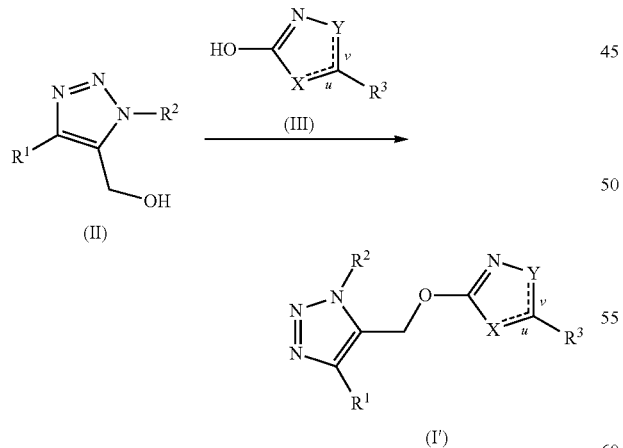

or
b) the reaction of a compound of formula (IV) with a compound of formula (V) to give a compound of formula (VI) followed by the subsequent reaction of a compound of formula (VI) to give a compound of formula (I") wherein A is —CH=CH—

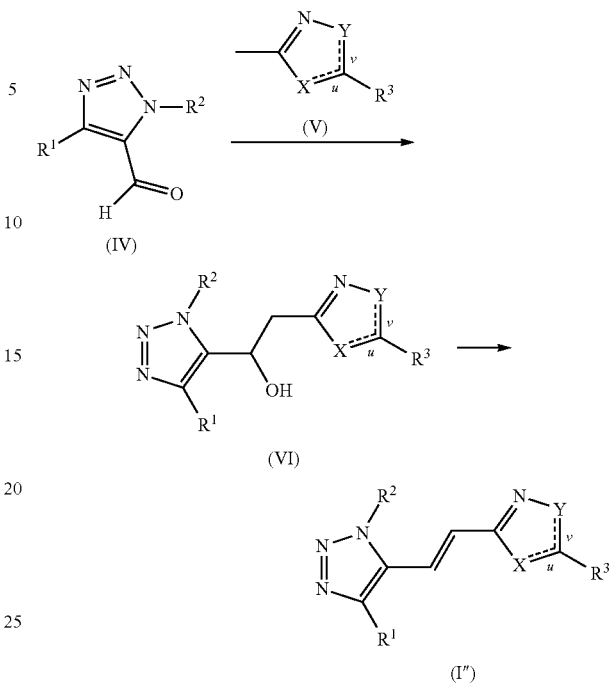

wherein X, Y, u, v, R$^1$, R$^2$ and R$^3$ are as defined herein.

The invention further provides compounds of formula (I) as defined above obtainable by a process as described above.

Compounds of formula (I) can be prepared following standard methods as described below, wherein A, X, Y, u, v, R$^1$, R$^2$ and R$^3$ are as described above and in the claims, unless mentioned otherwise.

The present compounds of formula (I') wherein A is —CH$_2$—O— and R$^2$ is alkyl and their pharmaceutically acceptable salts can be prepared in accordance to schemes 1 and 2.

Scheme 1

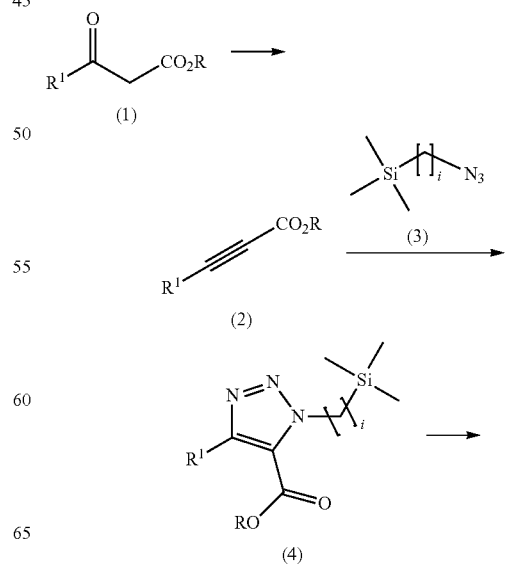

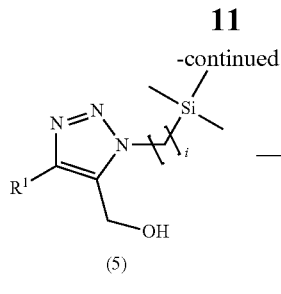

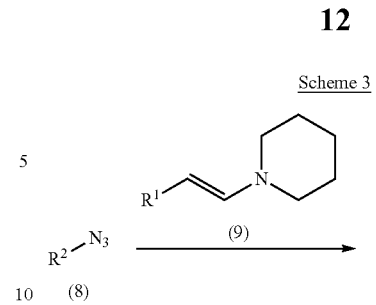

According to scheme 1, compounds of formula (1), wherein R is alkyl, can be reacted with triphenylphosphine oxide and Tf$_2$O in the presence of a base such as triethylamine in a suitable solvent such as 1,2-dichloroethane to give a compound of formula (2). Alternatively compounds of formula (1) can be treated with a strong base such as BuLi in the presence of ethyl chloroformate in a suitable solvent to give compounds of formula (2). Compounds of formula (2) can be reacted with a compound of formula (3), wherein i is an integer from 1 to 7, particularly 1, 2 or 4, most particularly 1, in a suitable solvent such as benzene upon heating to give a compound of formula (4). Compounds of formula (4) can be treated with a reducing agent such as lithiumaluminiumhydride in a suitable solvent such as THF to give a compound of formula (5). Compounds of formula (5) can be treated with TBAF in a suitable solvent such as THF in water to give a compound of formula (6).

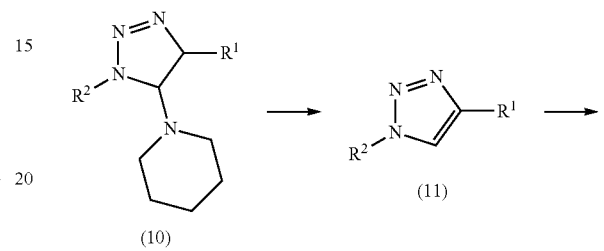

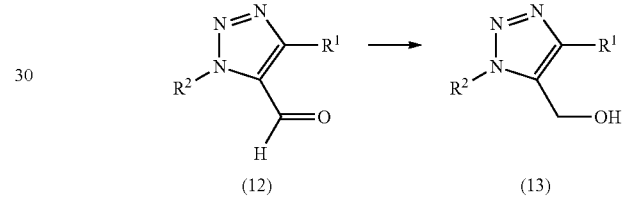

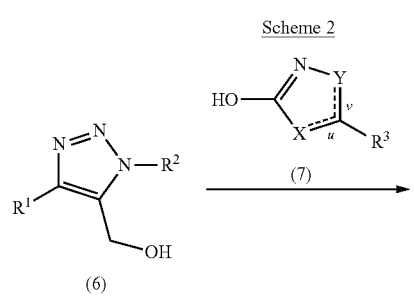

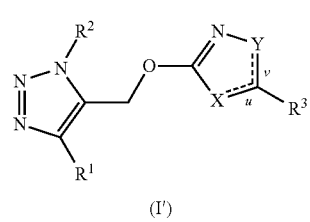

According to scheme 2, compounds of formula (6) can be reacted with compounds of formula (7) in the presence of triphenylphosphine and diethylazodicarboxylate, in a suitable solvent, such as THF to give a compound of formula (1') wherein A is —CH$_2$—O— and R$^2$ is alkyl.

The present compounds of formula (I') wherein A is —CH$_2$—O— and R$^1$ is alkyl and their pharmaceutically acceptable salts can be prepared according to schemes 3 and 2.

Compounds of formula (8) can be treated with compounds of formula (9) to give compounds of formula (10) which upon treatment with a base such as potassium hydroxide in a suitable solvent such as methanol gives compounds of formula (11). Compounds of formula (11) can then be treated with a strong base such as BuLi in a suitable solvent such as THF and then be reacted with DMF to give a compound of formula (12). Compounds of formula (12) can be treated with a reducing agent such as sodiumborohydride in a suitable solvent such as methanol to give a compound of formula (13). Compounds of formula (13) are equivalent to compounds of formula (6) in their subsequent reactivity and can be manipulated accordingly as shown above. The present compounds of formula (I') wherein A is —CH$_2$—O— and R$^1$ is alkyl and their pharmaceutically acceptable salts can be prepared from compounds of formula (13) according to Scheme 3.

The present compounds of formula (I'') wherein A is —CH═CH— and R$^2$ is alkyl and their pharmaceutically acceptable salts can be prepared according to schemes 4 and 5.

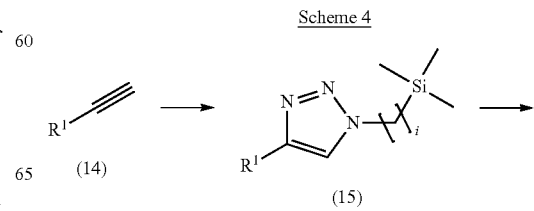

-continued

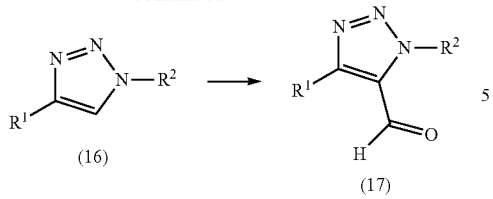

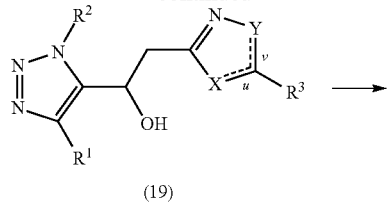

According to scheme 4, a compound of formula (14) is reacted with a compound of formula (3), wherein i is an integer from 1 to 7, particularly 1, 2 or 4, most particularly 1, in the presence of Cu(I)I in a suitable solvent such as DMF in the presence of a base such as DIPEA to give a compound of formula (15) which can then be treated with TBAF in a suitable solvent such as THF in water to give a compound of formula (16). Alternatively a compound of formula (14) can be treated with Cu(I)I with sodium azide and a compound of formula IR² (iodomethane) in the presence of ascorbic acid under activating conditions such as sonication to give a compound of formula (16). Compounds of formula (16) can then be treated with a strong base such as BuLi in a suitable solvent such as THF and then reacted with DMF to give a compound of formula (17).

Scheme 5

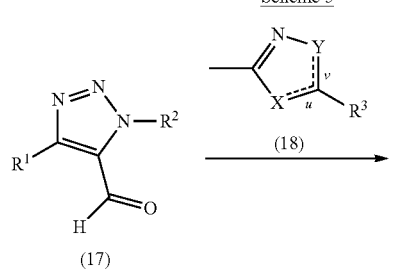

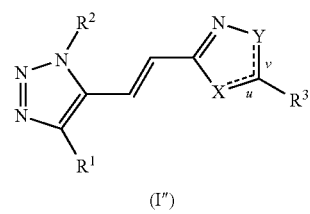

According to scheme 5, compounds of formula (17) can be reacted with compounds of formula (18) in the presence of a strong base such as BuLi in a suitable solvent such as THF to give a compound of formula (19). A compound of formula (19) can be treated with sulfuric acid to give compounds of formula (I″).

The present compounds of formula (I″) wherein A is —CH=CH— and $R^1$ is alkyl and their pharmaceutically acceptable salts can be prepared according to schemes 3 and 5. Compounds of formula (16) are equivalent to compounds of formula (17) in their subsequent reactivity and can be manipulated accordingly as shown above.

In accordance with scheme 6, compounds of formula (I) wherein $R^3$=—C(O)NR⁵R⁶ can be prepared following standard methods from compounds of formula (I) wherein $R^3$=—C(O)R⁴.

Scheme 6

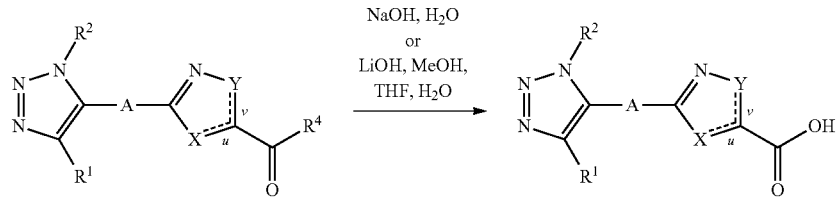

Me₃Al,
R⁵R⁶NH
dioxane
85-95° C.
1 h - on
or
TBD,
R⁵R⁶NH
toluene
r.t.-50° C.
1 h - 72 h TBTU, Hünigs Base
R⁵R⁶NH,
DMF, r.t., 1 h - on
or
CDI, 30 min, 80° C.
R⁵R⁶NH
DMF, 80° C., 1 h - on
or
EDAC, HOBt,
DIPEA, r.t.
R⁵R⁶NH
DCM, 1 h - on

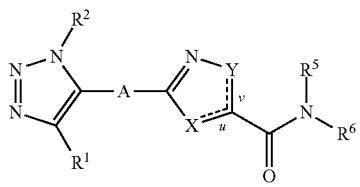

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also provides compounds of formula (I) as defined above, when prepared by a process as described above.

BuLi=n-butyllithium
CDI=1,1'-carbonyldiimidazole
DCM=dichloromethane
DIPEA=N,N-diisopropylethylamine (Hünigs Base)
DMF=dimethylformamid
EDAC=1-ethyl-3-(3-dimethylaminopropyl) carbodiimide hydrochloride
HOBt=hydroxybenzotriazole
hv=high vacuum
on=overnight
r.t.=room temperature
TBD=1,5,7-triazabicyclo[4.4.0]dec-5-ene
TBTU=O-(benzotriazol-1-yl)-N,N,N',N'-tetramethyluronium tetrafluoroborate
Tf₂O=trifluoromethanesulfonic anhydride
THF=tetrahydrofuran Another embodiment provides pharmaceutical compositions or medicaments containing the compounds of the invention and a therapeutically inert carrier, diluent or excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can contain components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution can be filtered, e.g., using a 0.2 μm filter, to remove impurities and contaminants.

As described above, the novel compounds of the present invention and their pharmaceutically acceptable salts possess valuable pharmacological properties and are ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also provides pharmaceutical compositions containing a compound as defined above and a pharmaceutically acceptable excipient.

The invention likewise embraces compounds as described above for use as therapeutically active substances.

The invention likewise embraces compounds as described above for use as therapeutically active substances for the treatment or prevention of diseases which are related to the GABA A α5 receptor.

The invention likewise embraces compounds as described above for use as therapeutically active substances for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

The invention likewise embraces compounds as described above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another embodiment, the invention provides a method for the treatment or prevention of diseases which are related to the GABA A α5 receptor.

In another embodiment, the invention provides a method for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor.

The invention also embraces the use of compounds as defined above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also provides the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

More particularly, the present invention provides the use of compounds as described above for the treatment, prevention and/or delay of progression of CNS conditions caused by neurodevelopmental defects which result in excessive GABAergic inhibition in the cortex and hippocampus, wherein the CNS condition is selected from cognitive deficits in Down Syndrome, in autism, in neurofibromatosis type I, or after stroke.

The treatment or prevention of cognitive disorders, Alzheimer's disease, schizophrenia, positive, negative and/or cognitive symptoms associated with schizophrenia, Down syndrome, and neurofibromatosis type I, are particular embodiments of present invention.

A particular embodiment of the invention embraces the treatment or prevention of Alzheimer's disease.

A particular embodiment of the invention embraces the treatment or prevention of Down syndrome.

A particular embodiment of the invention embraces the treatment or prevention of neurofibromatosis type I.

The invention will be more fully understood by reference to the following examples. They should not, however, be construed as limiting the scope of the invention.

Example 1

3-[5-(4-Fluoro-phenyl)-3-methyl-3H-[1,2,3]triazol-4-ylmethoxyl]isoxazole-5-carboxylic acid (tetrahydro-pyran-4-yl)-amide

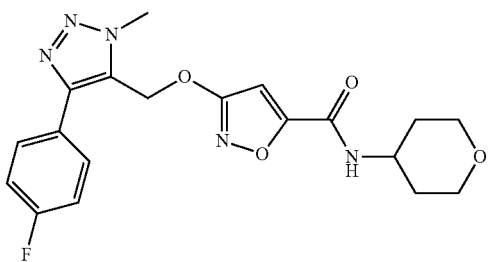 [SMILES: Cn1nnc(-c2ccc(F)cc2)c1COc1cc(C(=O)NC2CCOCC2)on1]

(4-Fluoro-phenyl)-propynoic acid ethyl ester

Prepared in analogy to *Synthesis Communications* (1989) 3:217-218. To a solution of triphenylphosphine oxide (3.77 g, 14 mmol) in 1,2-dichloroethane (42 mL) was added trifluoromethanesulfonic anhydride (2.25 mL, 14 mmol) dropwise at 0° C. and the grey suspension was stirred at 0° C. for 15 min. Then a solution of 3-(4-fluoro-phenyl)-3-oxo-propionic acid ethyl ester (2.85 g, 14 mmol) in 1,2-dichloroethane (14 mL) was added followed by a dropwise addition of triethylamine (3.78 mL, 28 mmol) at 0° C. The brown solution was refluxed for 2.5 h. After cooling the mixture was poured onto ice-water and the organic layer separated and washed with brine, dried over sodium sulphate, filtered and evaporated. Purification by chromatography (silica, 0 to 20% ethyl acetate in heptane) afforded the title compound (1.53 g, 59%) as a yellow solid. MS: m/e=193.2 [M+H]$^+$.

b) 5-(4-Fluoro-phenyl)-3-trimethylsilanylmethyl-3H-[1,2,3]triazole-4-carboxylic acid ethyl ester To a solution of (4-fluoro-phenyl)-propynoic acid ethyl ester (1.45 g, 7.55 mmol) in benzene (25 mL) was added azidomethyl-trimethyl-silane (1.17 g, 9.05 mmol) and the reaction mixture was refluxed under nitrogen for 72 h. A subsequent batch of azidomethyl-trimethyl-silane (0.29 g, 2.26 mmol) was added and refluxing was continued for 5 h. The mixture was then evaporated and purification by chromatography (silica, 0 to 50% ethyl acetate in heptane) afforded the title compound (1.0 g, 41%) as a yellow oil. MS: m/e=322.2 [M+H]$^+$.

c) [5-(4-Fluoro-phenyl)-3-trimethylsilanylmethyl-3H-[1,2,3]triazol-4-yl]-methanol To a solution of 5-(4-fluoro-phenyl)-3-trimethylsilanylmethyl-3H-[1,2,3]triazole-4-carboxylic acid ethyl ester (880 mg, 2.74 mmol) in dry THF (8.2 mL) was added portionwise lithiumaluminiumhydride (119 mg, 3.15 mmol) at 0° C. and the reaction mixture was stirred at 0° C. for 1 h. Then water (119 µL) and NaOH (15%, 119 µL) was added followed by water (357 µL). The precipitate was then filtered off and the filtrate evaporated. Purification by chromatography (silica, 0 to 100% ethyl acetate in heptane) afforded the title compound (649 mg, 85%) as a white solid. MS: m/e=280.1 [M+H]$^+$.

d) [5-(4-Fluoro-phenyl)-3-methyl-3H-[1,2,3]triazol-4-yl]-methanol

To a solution of [5-(4-fluoro-phenyl)-3-trimethylsilanylmethyl-3H-[1,2,3]triazol-4-yl]-methanol (616 mg, 2.20 mmol) in THF (37 mL) was added water (79 µL, 4.41 mmol) and then tetrabutylammonium fluoride (1 M in THF, 2.65 mL, 2.65 mmol) added dropwise at 0° C. The reaction mixture was stirred at 0° C. for 15 min. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 0 to 100% ethyl acetate in heptane) afforded the title compound (410 mg, 90%) as an off white solid. MS: m/e=208.0 [M+H]$^+$.

e) Methyl 3-[5-(4-Fluoro-phenyl)-3-methyl-3H-[1,2,3]-triazol-4-ylmethoxy]-isoxazole-5-carboxylate To a solution of [5-(4-fluoro-phenyl)-3-methyl-3H-[1,2,3]triazol-4-yl]-methanol (290 mg, 1.4 mmol) in THF (30 mL) was added methyl 3-hydroxy 5-isoxazolecarboxylate (200 mg, 1.4 mmol) and triphenylphosphine (477 mg, 1.82 mmol) at ambient temperature under an argon atmosphere. Then diethyl azodicarboxylate (641 µL, 3.5 mmol) was added and the reaction mixture was stirred for 72 h at room temperature. Concentration and purification by chromatography (silica, 20 to 50% ethyl acetate in heptane) afforded the title compound (464 mg, 100%) as a white solid. MS: m/e=333.2 [M+H]$^+$.

f) 3-[5-(4-Fluoro-phenyl)-3-methyl-3H-[1,2,3]triazol-4-ylmethoxy]-isoxazole-5-carboxylic acid A solution of sodium hydroxide (2 N, 10 mL) was added dropwise to a suspension of methyl 3-[5-(4-Fluoro-phenyl)-3-methyl-3H-[1,2,3]triazol-4-ylmethoxy]-isoxazole-5-carboxylate (460 mg, 1.38 mmol) in dioxane (20 mL) and the reaction mixture was then heated at 90° C. for 1.5 h. The reaction mixture was then evaporated and acidified with HCl (2N), and the resulting precipitate filtered off to afford the title product (320 mg, 73%) as a white solid and used directly in the next step.

g) 3-[5-(4-Fluoro-phenyl)-3-methyl-3H-[1,2,3]-triazol-4-ylmethoxy]-isoxazole-5-carboxylic acid (tetrahydro-pyran-4-yl)-amide To a solution of 3-[5-(4-fluoro-phenyl)-3-methyl-3H-[1,2,3]triazol-4-ylmethoxy]-isoxazole-5-carboxylic acid (40 mg, 0.13 mmol) and TBTU (64.6 mg, 0.20 mmol) in DMF (2.0 mL) was added DIPEA (106.9 µL, 0.63 mmol). Then 4-aminotetrahydropyran (14 mg, 0.14 mmol) was added and the mixture was stirred at room temperature under Ar for 1 h. The mixture was then evaporated and purification by chromatography (silica, 50 to 100% ethyl acetate in heptane) afforded the title compound (35 mg, 70%) as a white solid. MS: m/e=402.2 [M+H]+.

Example 2

5-[5-(4-Fluoro-phenyl)-3-methyl-3H-[1,2,3]triazol-4-ylmethoxy]-2-methyl-2H-pyrazole-3-carboxylic acid (tetrahydro-pyran-4-yl)-amide

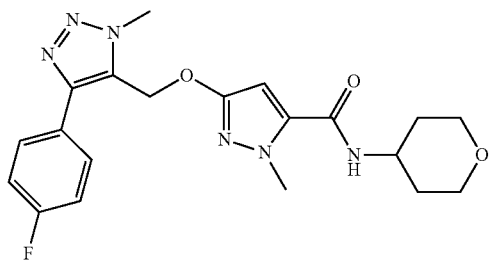 [SMILES: Cn1nc(OCc2c(-c3ccc(F)cc3)nnn2C)cc1C(=O)NC1CCOCC1]

a) Methyl 5-[5-(4-fluoro-phenyl)-3-methyl-3H-[1,2,3]triazol-4-ylmethoxy]-2-methyl-2H-pyrazole-3-carboxylate To a solution of [5-(4-fluoro-phenyl)-3-methyl-3H-[1,2,3]triazol-4-yl]-methanol (290 mg, 1.4 mmol) in THF (30 mL) was added 5-hydroxy-2-methyl-2H-pyrazole-3-carboxylic acid methyl ester (218 mg, 1.4 mmol) and triphenylphosphine (477 mg, 1.82 mmol) at ambient temperature under an argon atmosphere. Then diethyl azodicarboxylate (641 µL, 3.5 mmol) was added and the reaction mixture was stirred for 16 h at room temperature. Concentration and purification by chromatography (silica, 20 to 50% ethyl acetate in heptane) afforded the title compound (483 mg, 100%) as a white solid. MS: m/e=346.2 [M+H]+.

b) 5-[5-(4-Fluoro-phenyl)-3-methyl-3H-[1,2,3]triazol-4-ylmethoxy]-2-methyl-2H-pyrazole-3-carboxylic acid A solution of sodium hydroxide (2 N, 10 mL) was added dropwise to a suspension of NAME (480 mg, 1.39 mmol) in dioxane (20 mL) and the reaction mixture was then heated at 90° C. for 1.5 h. The reaction mixture was then evaporated and acidified with HCl (2N), and the resulting precipitate filtered off to afford the title product (340 mg, 74%) as a white solid and used directly in the next step. MS: m/e=330.2 [M+H]+.

c) 5-[5-(4-Fluoro-phenyl)-3-methyl-3H-[1,2,3]triazol-4-ylmethoxy]-2-methyl-2H-pyrazole-3-carboxylic acid (tetrahydro-pyran-4-yl)-amide To a solution of name (40 mg, 0.13 mmol) and TBTU (64.6 mg, 0.20 mmol) in DMF (2.0 mL) was added DIPEA (106.9 µL, 0.63 mmol). Then 4-aminotetrahydropyran (13 mg, 0.13 mmol) was added and the mixture was stirred at room temperature under Ar for 1 h. The mixture was then evaporated and purification by chromatography (silica, 50 to 100% ethyl acetate in heptane) afforded the title compound (42 mg, 85%) as a white solid. MS: m/e=415.2 [M+H]+.

Example 3

5-[3-(4-Fluoro-phenyl)-5-methyl-3H-[1,2,3]triazol-4-ylmethoxy]-2-methyl-2H-pyrazole-3-carboxylic acid (tetrahydro-pyran-4-yl)-amide

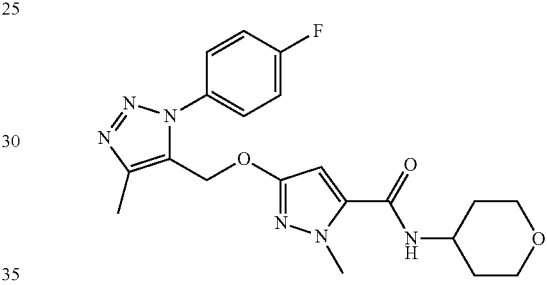

a) 1-Azido-4-fluoro-benzene

Prepared in analogy to J. Org. Chem. (1989) 54:5938-5945. To a solution of sulfuric acid (40 mL) and trifluoroacetic acid (200 mL) was added 4-fluoroaniline (22.1 mL, 0.23 mol) dropwise. Then under ice-cooling a solution of sodium nitrite (20.6 g, 0.3 mol) in water (200 mL) was added over 30 min at 15-18° C. The solution was then stirred for 30 min while kept in the ice bath. A solution of sodium azide (25.42 g, 0.39 mol) in water (150 mL) was added dropwise over 30 min. Mixture was foaming and temperature went up to 10° C. while cooling with an ice bath. Reaction mixture was stirred without cooling for 1 h, then extracted with diethyl ether. The combined organic layers were washed with water two times. Then the combined organic layers were diluted with saturated aqueous sodium carbonate solution (500 mL) until the mixture became basic. The organic phase was separated and washed with brine, extracted again with diethyl ether. The organic layers were dried over sodium sulfate and evaporated at 40° C., minimum 50 mbar (already distillation of product), to afford the title product (30.42 g, 96%) as a brown liquid.

b) 1-[3-(4-Fluoro-phenyl)-5-methyl-4,5-dihydro-3H-[1,2,3]triazol-4-yl]-piperidine Prepared in analogy to EP 0 433 842 A2. A mixture of 1-azido-4-fluoro-benzene (2.80 g, 20 mmol) and 1-(1-propenyl)-piperidine (18%, 14.2 g, 20 mmol) was stirred under ice cooling (slowly exothermic in the beginning) and at room temperature for 144 h in the absence of light. Hexane was then added to the brown solutions and a solid formed which was filtered off, washed with hexane and dried in hv to give the title product (1.1 g) as a light pink solid. The filtrate was then evaporated and purification by chromatography (silica, 10 to 50% ethyl acetate in heptane) afforded the title compound (4.34 g) as a light yellow solid. Total yield (5.44 g, 98%). MS: m/e=263.1 [M+H]$^+$.

c) 1-(4-Fluoro-phenyl)-4-methyl-1H-[1,2,3]triazole

Prepared in analogy to EP 0 433 842 A2. A mixture of 1-[3-(4-fluoro-phenyl)-5-methyl-4,5-dihydro-3H-[1,2,3] triazol-4-yl]-piperidine (1.15 g, 0.004 mol) and potassium hydroxide in MeOH (2 N, 29.2 mL, 58 mmol) was heated under reflux for 6 h then cooled to room temperature. The mixture was then poured into water and extracted with diethyl ether and the combined organic extracts washed with brine, dried over sodium sulphate, filtered and evaporated to give the title product (555 mg) as a white solid. The filtrate was evaporated and purification by chromatography (silica, 10 to 60% ethyl acetate in heptane) afforded the title compound (41 mg, 79%) as an off white solid. Total yield (596 mg, 77%). MS: m/e=178.1 [M+H]$^+$.

d) 3-(4-Fluoro-phenyl)-5-methyl-3H-[1,2,3]triazole-4-carbaldehyde

To a solution of 1-(4-fluoro-phenyl)-4-methyl-1H-[1,2,3] triazole (3.67 g, 21 mmol) in THF (110 mL) was added n-BuLi (1.6 M in hexane, 15.53 mL, 25 mmol) dropwise at −75° C. under Argon. The resulting solution was stirred at −75° C. for 1 h, then DMF (2.1 mL, 27 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (3.85 g, 91%) as a white solid. MS: m/e=206.2 [M]$^+$.

e) [3-(4-Fluoro-phenyl)-5-methyl-3H-[1,2,3]triazol-4-yl]-methanol

To a solution of 3-(4-fluoro-phenyl)-5-methyl-3H-[1,2,3] triazole-4-carbaldehyde (2.28 g, 11 mmol) in MeOH (180 mL) was added sodiumborohydride (210 mg, 6.0 mmol) at 0° C., and the resulting mixture stirred at 0° C. for 30 min, The mixture was then poured into saturated ammonium chloride solution and extracted with ethyl acetate and the combined organic extracts washed with brine, dried over sodium sulphate, filtered and evaporated to afford the title compound (2.05 g, 89%) as a white solid. MS: m/e=208.2 [M]$^+$.

f) 5-[3-(4-Fluoro-phenyl)-5-methyl-3H-[1,2,3]triazol-4-ylmethoxy]-2-methyl-2H-pyrazole-3-carboxylic acid methyl ester To a solution of [3-(4-fluoro-phenyl)-5-methyl-3H-[1,2,3] triazol-4-yl]-methanol (500 mg, 2 mmol) in THF (30 mL) was added 5-hydroxy-2-methyl-2H-pyrazole-3-carboxylic acid methyl ester (377 mg, 2 mmol) and triphenylphosphine (823 mg, 3 mmol) at ambient temperature under an argon atmosphere. Then diethyl azodicarboxylate (~40% in toluene, 1.44 mL, 3 mmol) was added and the reaction mixture was stirred for 24 h at room temperature. Concentration and purification by chromatography (silica, 20 to 50% ethyl acetate in heptane and then 2% methanol in dichloromethane) afforded the title compound (671 mg, 81%) as a white solid. MS: m/e=346.1 [M+H]$^+$.

g) 5-[3-(4-Fluoro-phenyl)-5-methyl-3H-[1,2,3]-triazol-4-ylmethoxy]-2-methyl-2H-pyrazole-3-carboxylic acid A solution of lithium hydroxide monohydrate (146 mg, 3.48 mmol) in water (6 mL) was added dropwise to a suspension of 5-[3-(4-fluoro-phenyl)-5-methyl-3H-[1,2,3]triazol-4-ylmethoxy]-2-methyl-2H-pyrazole-3-carboxylic acid methyl ester (600 mg, 1.74 mmol) in THF (6 mL). The reaction mixture was then stirred at room temperature for 2 h and was then evaporated and the residue dissolved in water, acidified with HCl (1N), and the resulting precipitate filtered off to afford the title product (544 mg, 95%) as a white solid. MS: m/e=330.2 [M−H]$^-$.

h) 5-[3-(4-Fluoro-phenyl)-5-methyl-3H-[1,2,3]triazol-4-ylmethoxy]-2-methyl-2H-pyrazole-3-carboxylic acid (tetrahydro-pyran-4-yl)-amide To a solution of 5-[3-(4-fluoro-phenyl)-5-methyl-3H-[1,2, 3]triazol-4-ylmethoxy]-2-methyl-2H-pyrazole-3-carboxylic acid (85 mg, 0.26 mmol) and TBTU (91 mg, 0.28 mmol) in DMF (3.0 mL) was added DIPEA (220 µL, 1.28 mmol). Then 4-aminotetrahydropyran (29 mg, 0.28 mmol) was added and the mixture was stirred at room temperature under Ar for 30 min. The mixture was then evaporated and purification by chromatography (silica, 50 to 100% ethyl acetate in heptane) afforded the title compound (72 mg, 68%) as a white solid. MS: m/e=415.4 [M+H]$^+$.

Example 4

5-[3-(4-Fluoro-phenyl)-5-methyl-3H-[1,2,3]triazol-4-ylmethoxy]-2-methyl-2H-pyrazole-3-carboxylic acid morpholin-4-ylamide

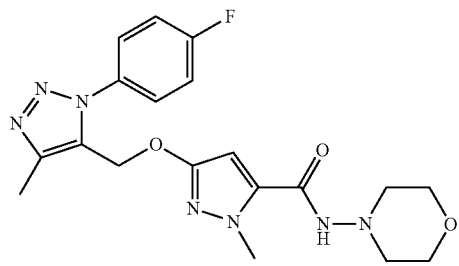 [SMILES: Cc1nnn(-c2ccc(F)cc2)c1COc1cc(C(=O)NN2CCOCC2)n(C)n1]

As described for example 3, 5-[3-(4-fluoro-phenyl)-5-methyl-3H-[1,2,3]triazol-4-ylmethoxy]-2-methyl-2H-pyrazole-3-carboxylic acid (85 mg, 0.26 mmol), was converted, using 4-aminomorpholine instead of 4-aminotetrahydropy-

Example 5

5-[3-(4-Fluoro-phenyl)-5-methyl-3H-[1,2,3]triazol-4-ylmethoxy]-2-methyl-2H-pyrazole-3-carboxylic acid (3-methyl-oxetan-3-yl)-amide

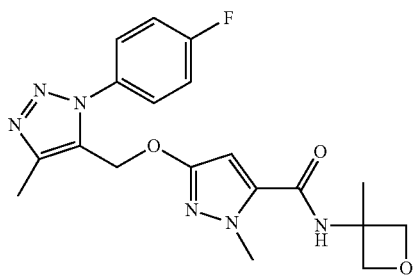 [SMILES: Cc1nnn(-c2ccc(F)cc2)c1COc1cc(C(=O)NC2(C)COC2)n(C)n1]

As described for example 3, 5-[3-(4-fluoro-phenyl)-5-methyl-3H-[1,2,3]triazol-4-ylmethoxy]-2-methyl-2H-pyrazole-3-carboxylic acid (85 mg, 0.26 mmol), was converted, using 3-methyl-3-oxetanamine instead of 4-aminotetrahydropyran, to the title compound (98 mg, 95%) which was obtained as a white solid. MS: m/e=401.3 [M+H]$^+$.

Example 6

2-{(E)-2-[5-(4-Fluoro-phenyl)-3-methyl-3H-[1,2,3]triazol-4-yl]vinyl}-4-methyl-thiazole-5-carboxylic acid isopropylamide

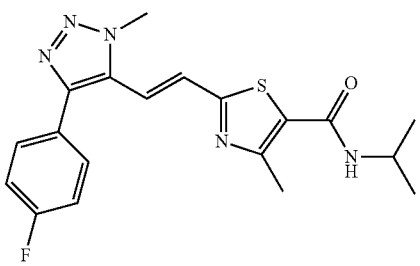 [SMILES: Cc1nc(/C=C/c2c(-c3ccc(F)cc3)nnn2C)sc1C(=O)NC(C)C]

a) 4-(4-Fluoro-phenyl)-1-trimethylsilanylmethyl-1H-[1,2,3]triazole

To a suspension of copper(I)iodide (1.14 g, 20 mol %) in DMF (300 mL) was added DIPEA (5.14 mL, 6.0 mmol) and 4-fluorophenylacetylene (3.60 g 30 mmol) at room temperature and then trimethyl(triazomethyl)silane (3.88 g, 30.0 mmol) was added. The resulting reaction mixture was stirred at room temperature for 18 h. The mixture was poured into water:brine (1:1) and then extracted with ethyl acetate. The combined organic extracts were then washed with brine, dried over sodium sulphate, filtered and evaporated. Purification by chromatography (silica, 0 to 100% ethyl acetate in heptane) afforded the title compound (5.96 g, 80%) as an off white solid. MS: m/e=250.1 [M+H]$^+$.

b) 4-(4-Fluoro-phenyl)-1-methyl-1H-[1,2,3]triazole

To a solution of 4-(4-fluoro-phenyl)-1-trimethylsilanylmethyl-1H-[1,2,3]triazole (5.80 g, 23 mmol) in THF (85 mL) was added water (840 µL, 47 mmol) and then tetrabutylammonium fluoride (1 M in THF, 27.9 mL, 28 mmol) was added dropwise at 0° C. The reaction mixture was stirred at 0° C. for 1 h. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 50 to 100% ethyl acetate in heptane) afforded the title compound (4.0 g, 98%) as an off white solid. MS: m/e=178.1 [M+H]$^+$.

c) 5-(4-Fluoro-phenyl)-3-methyl-3H-[1,2,3]triazole-4-carbaldehyde

To a solution of 4-(4-fluoro-phenyl)-1-methyl-1H-[1,2,3]triazole (709 mg, 4.0 mmol) in THF (20 mL) was added n-BuLi (1.6 M in hexane, 3.0 mL, 4.8 mmol) dropwise at −75° C. under Argon. The resulting solution was stirred at −75° C. for 1 h, then DMF (401 µL, 5.2 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (773 mg, 94%) as a white solid. MS: m/e=206.2 [M]$^+$.

d) 2-{2-[5-(4-Fluoro-phenyl)-3-methyl-3H-[1,2,3]triazol-4-yl]-2-hydroxy-ethyl}-4-methyl-thiazole-5-carboxylic acid methyl ester To a suspension of 2,4-dimethylthiazole-5-carboxylic acid (236 mg, 1.5 mmol) in THF (12 mL) was added dropwise n-BuLi (1.6 M in hexanes, 1.88 mL, 3.0 mmol) under Ar at −75° C. The brown suspension was stirred at −75° C. for 2 h and then a solution of 5-(4-fluoro-phenyl)-3-methyl-3H-[1,2,3]triazole-4-carbaldehyde (308 mg, 1.50 mmol) in THF (4.5 mL) was added at −75° C. and the brown suspension was stirred at −75° C. for 2 h. The mixture was then quenched with an aqueous solution of citric acid (5%, 15 mL), allowed to warm to room temperature. The mixture was then poured into saturated ammonium chloride solution and extracted with ethyl acetate and the combined organic extracts washed with brine, dried over sodium sulphate, filtered and evaporated. Purification by chromatography (silica, 0 to 30% methanol in dichloromethane) afforded 2-{2-[5-(4-fluoro-phenyl)-3-methyl-3H-[1,2,3]triazol-4-yl]-2-hydroxy-ethyl}-4-methyl-thiazole-5-carboxylic acid (417 mg, 77%) as a yellow foam. The acid was then dissolved in methanol (4 mL) and diethylether (2 mL) and trimethylsilyldiazomethane (2M in diethylether, 5×0.38 mL, 3.75 mmol) added dropwise. The reaction was quenched with a few drops of AcOH and evaporated. To the brown oil was added sodium hydroxide (1 N, 20 mL) and extracted with ethyl acetate. The combined organic layers were washed with brine, dried over sodium sulfate and evaporated. Purification by chromatography (silica, 0 to 30% methanol in dichloromethane) afforded the title compound (214 mg, 38%) as a light brown foam.

MS: m/e=377.3 [M+H]$^+$.

e) 2-{(E)-2-[5-(4-Fluoro-phenyl)-3-methyl-3H-[1,2,3]triazol-4-yl]-vinyl}-4-methyl-thiazole-5-carboxylic acid A suspension of 2-{2-[5-(4-fluoro-phenyl)-3-methyl-3H-[1,2,3]triazol-4-yl]-2-hydroxy-ethyl}-4-methyl-thiazole-5-carboxylic acid methyl ester (204 mg, 0.54 mmol) in sulfuric acid (conc., 3.19 mL) was heated at 160° C. under Ar for 2 h. After cooling to room temperature the mixture was poured into ice and extracted with ethyl acetate and the combined organic extracts washed with brine, dried over sodium sulphate, filtered and evaporated to afford the title compound (165 mg, 88%) as an off white solid. MS: m/e=343.0 [M−H]⁻.

f) 2-{(E)-2-[5-(4-Fluoro-phenyl)-3-methyl-3H-[1,2,3]triazol-4-yl]-vinyl}-4-methyl-thiazole-5-carboxylic acid isopropylamide To a solution of 2-{(E)-2-[5-(4-fluoro-phenyl)-3-methyl-3H-[1,2,3]triazol-4-yl]-vinyl}-4-methyl-thiazole-5-carboxylic acid (75 mg, 0.22 mmol) and TBTU (77 mg, 0.24 mmol) in DMF (0.4 mL) was added DIPEA (186 µL, 1.09 mmol). Then isopropylamine (21 µL, 0.24 mmol) was added and the mixture was stirred at room temperature under Ar for 1 h. The mixture was then evaporated and purification by chromatography (silica, 1 to 5% methanol in dichloromethane) afforded the title compound (28 mg, 33%) as an off white solid after recrystallisation from ethylacetate and heptane. MS: m/e=386.4 [M+H]⁺.

Example 7

2-{(E)-2-[5-(4-Fluoro-phenyl)-3-methyl-3H-[1,2,3]triazol-4-yl]-vinyl}-4-methyl-thiazole-5-carboxylic acid (tetrahydro-pyran-4-yl)-amide

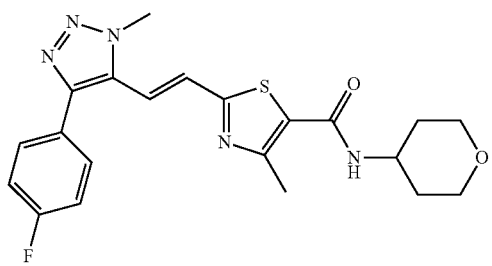 [SMILES: Cc1nc(/C=C/c2c(-c3ccc(F)cc3)nnn2C)sc1C(=O)NC1CCOCC1]

As described for example 6f, 2-{(E)-2-[5-(4-fluoro-phenyl)-3-methyl-3H-[1,2,3]triazol-4-yl]-vinyl}-4-methyl-thiazole-5-carboxylic acid (75 mg, 0.22 mmol), was converted, using 4-aminotetrahydropyran instead of isopropylamine, to the title compound (63 mg, 68%) which was obtained as a light yellow solid. MS: m/e=428.3 [M+H]⁺.

Example 8

2-{(E)-2-[3-(4-Fluoro-phenyl)-5-methyl-3H-[1,2,3]triazol-4-yl]-vinyl}-4-methyl-thiazole-5-carboxylic acid (tetrahydro-pyran-4-yl)-amide

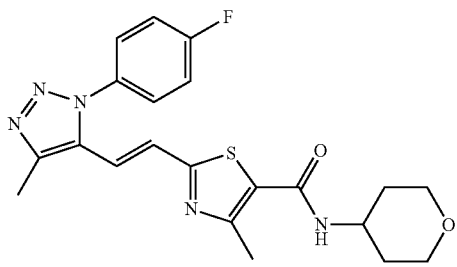 [SMILES: Cc1nc(/C=C/c2c(C)nnn2-c2ccc(F)cc2)sc1C(=O)NC1CCOCC1]

a) 2-{2-[3-(4-Fluoro-phenyl)-5-methyl-3H-[1,2,3]triazol-4-yl]-2-hydroxy-ethyl}-4-methyl-thiazole-5-carboxylic acid methyl ester As described for example 7d, 3-(4-fluoro-phenyl)-5-methyl-3H-[1,2,3]triazole-4-carbaldehyde (630 mg, 3.1 mmol), was converted, instead of 5-(4-fluoro-phenyl)-3-methyl-3H-[1,2,3]triazole-4-carbaldehyde to the title compound (392 mg, 34%) which was obtained as a light brown solid. MS: m/e=377.3 [M+H]⁺.

b) 2-{(E)-2-[3-(4-Fluoro-phenyl)-5-methyl-3H-[1,2,3]triazol-4-yl]-vinyl}-4-methyl-thiazole-5-carboxylic acid A suspension of 2-{2-[3-(4-fluoro-phenyl)-5-methyl-3H-[1,2,3]triazol-4-yl]-2-hydroxy-ethyl}-4-methyl-thiazole-5-carboxylic acid methyl ester (355 mg, 0.94 mmol) in sulfuric acid (conc, 5.9 mL) was heated at 160° C. under Ar for 30 min. After cooling to room temperature the mixture was poured into ice and extracted with ethyl acetate and the combined organic extracts washed with brine, dried over sodium sulphate, filtered and evaporated to afford the title compound (249 mg, 77%) as an grey solid. MS: m/e=345.1 [M+H]⁺.

c) 2-{(E)-2-[3-(4-Fluoro-phenyl)-5-methyl-3H-[1,2,3]triazol-4-yl]-vinyl}-4-methyl-thiazole-5-carboxylic acid (tetrahydro-pyran-4-yl)-amide To a solution of 2-{(E)-2-[3-(4-fluoro-phenyl)-5-methyl-3H-[1,2,3]triazol-4-yl]-vinyl}-4-methyl-thiazole-5-carboxylic acid (72 mg, 0.21 mmol) and TBTU (74 mg, 0.23 mmol) in DMF (3 mL) was added DIPEA (178 µL, 1.05 mmol). Then 4-aminotetrahydropyran (23 mg, 0.23 mmol) was added and the mixture was stirred at room temperature under Ar for 2 h. The mixture was then evaporated and purification by chromatography (silica, 30 to 80% ethylacetate in

Example 9

2-{(E)-2-[3-(4-Fluoro-phenyl)-5-methyl-3H-[1,2,3]triazol-4-yl]-vinyl}-4-methyl-thiazole-5-carboxylic acid isopropylamide

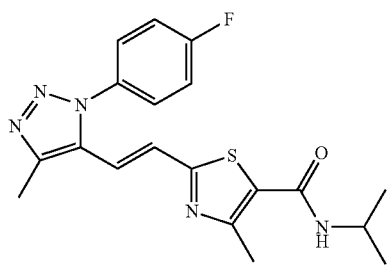 [SMILES: Cc1nc(/C=C/c2c(C)nnn2-c2ccc(F)cc2)sc1C(=O)NC(C)C]

As described for example 8c, 2-{(E)-2-[3-(4-fluoro-phenyl)-5-methyl-3H-[1,2,3]triazol-4-yl]-vinyl}-4-methyl-thiazole-5-carboxylic acid (72 mg, 0.21 mmol), was converted, using isopropylamine instead of 4-aminotetrahydropyran, to the title compound (57 mg, 71%) which was obtained as an off white solid. MS: m/e=386.4 [M+H]$^+$.

Example 10

4-Methyl-2-[(E)-2-(3-methyl-5-pyridin-2-yl-3H-[1,2,3]triazol-4-yl)-vinyl]-thiazole-5-carboxylic acid isopropylamide

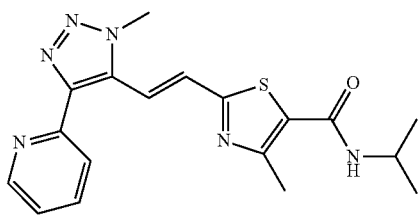 [SMILES: Cc1nc(/C=C/c2c(-c3ccccn3)nnn2C)sc1C(=O)NC(C)C]

a) 2-Ethynyl-pyridine

To a mixture of 2-pyridinecarbaldehyde (0.96 mL, 10 mmol) in MeOH (43 mL) was added potassium carbonate (2.76 g, 20 mmol) followed by a solution of (1-diazo-2-oxo-propyl)-phosphonic acid dimethyl ester (2.14 g, 11 mmol) in MeOH (14 mL) at room temperature and the resulting mixture stirred for 1.5 h. The mixture was then poured into sodium carbonate solution (1 M) and extracted with ethyl acetate and the combined organic extracts washed with brine, dried over sodium sulphate, filtered and evaporated. Purification by chromatography (silica, diethylether) afforded the title compound (728 mg, 71%) as a yellow liquid. MS: m/e=103.0 [M]$^+$.

b) 2-(1-Trimethylsilanylmethyl-1H-[1,2,3]triazol-4-yl)-pyridine

To a suspension of copper(I)iodide (1.36 g, 20 mol %) in DMF (360 mL) was added DIPEA (6.31 mL, 36 mmol) and 2-ethynyl-pyridine (110 μL. 1.00 mmol) at room temperature and then trimethyl(triazomethyl)silane (3.69 g, 36 mmol) was added. The resulting reaction mixture was stirred at room temperature for 18 h. The mixture was poured into water: brine (1:1) and then extracted with ethyl acetate. The combined organic extracts were then washed with brine, dried over sodium sulphate, filtered and evaporated. Purification by chromatography (silica, 0 to 50% ethyl acetate in heptane) afforded the title compound (6.05 g, 73%) as a light yellow solid. MS: m/e=233.1 [M+H]$^+$.

c) 2-(1-Methyl-1H-[1,2,3]triazol-4-yl)-pyridine

To a solution of 2-(1-trimethylsilanylmethyl-1H-[1,2,3]triazol-4-yl)-pyridine (6.05 g, 26 mmol) in THF (435 mL) was added water (0.94 mL, 52 mmol) and then tetrabutylammonium fluoride (1 M in THF, 31.2 mL, 31 mmol) was added dropwise at 0° C. The reaction mixture was stirred at 0° C. for 1 h. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 0 to 100% ethyl acetate in heptane) afforded the title compound (3.53 g, 85%) as a light brown solid. MS: m/e=161.2 [M+H]$^+$.

d) 3-Methyl-5-pyridin-2-yl-3H-[1,2,3]-triazole-4-carbaldehyde

To a solution of 2-(1-methyl-1H-[1,2,3]triazol-4-yl)-pyridine (3.52 g, 22 mmol) in THF (112 mL) was added n-BuLi (1.6 M in hexane, 16.5 mL, 4.96 mmol) dropwise at −75° C. and under Ar. The resulted light brown suspension was stirred at −75° C. for 1 h. Then DMF (2.20 mL, 29 mmol) was added dropwise at −75° C. and the yellow solution was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (3.75 g, 91%) as a white solid. MS: m/e=188.0 [M]$^+$.

e) 2-[2-Hydroxy-2-(3-methyl-5-pyridin-2-yl-3H-[1,2,3]triazol-4-yl)-ethyl]-4-methyl-thiazole-5-carboxylic acid To a suspension of 2,4-dimethylthiazole-5-carboxylic acid (157 mg, 1.0 mmol) in THF (8 mL) was added dropwise n-BuLi (1.6 M in hexanes, 1.25 mL, 2.0 mmol) under Ar at −75° C. The brown suspension was stirred at −75° C. for 2 h and then a solution of 3-methyl-5-pyridin-2-yl-3H-[1,2,3]triazole-4-carbaldehyde (188 mg, 1.0 mmol) in THF (3 mL) was added at −75° C. and the brown suspension was stirred at −75° C. for 2 h. The mixture was then quenched with an aqueous solution of citric acid (5%, 10 mL), allowed to warm to room temperature. The mixture was then poured into saturated ammonium chloride solution and extracted with ethyl acetate and the combined organic extracts washed with brine, dried over sodium sulphate, filtered and evaporated. Purification by recrystallisation from ethylacetate-heptane afforded the title compound (288 mg, 83%) as a light red solid. MS: m/e=344.0 [M−H]$^−$.

f) 4-Methyl-2-[(E)-2-(3-methyl-5-pyridin-2-yl-3H-[1,2,3]triazol-4-yl)-vinyl]-thiazole-5-carboxylic acid A suspension of 2-[2-hydroxy-2-(3-methyl-5-pyridin-2-yl-3H-[1,2,3]triazol-4-yl)-ethyl]-4-methyl-thiazole-5-carboxylic acid (152 mg, 0.44 mmol) in sulfuric acid (conc., 2.59 mL, 48.4 mmol) was heated at 160° C. under Ar for 7 h. After cooling to room temperature the mixture was poured into ice, adjusted to pH 4 with NaOH (6 N) and extracted with ethyl acetate and the combined organic extracts washed with brine, dried over sodium sulphate, filtered and evaporated to afford the title compound (114 mg, 79%) as an a yellow solid after trituration from methanol-water. MS: m/e=326.2 [M–H]⁻.

g) 4-Methyl-2-[(E)-2-(3-methyl-5-pyridin-2-yl-3H-[1,2,3]-triazol-4-yl)-vinyl]-thiazole-5-carboxylic acid isopropylamide To a solution of 4-methyl-2-[(E)-2-(3-methyl-5-pyridin-2-yl-3H-[1,2,3]triazol-4-yl)-vinyl]-thiazole-5-carboxylic acid (56 mg, 0.17 mmol) and TBTU (60 mg, 0.19 mmol) in DMF (0.9 mL) was added DIPEA (146 µL, 0.86 mmol). Then isopropylamine (16 µL, 0.24 mmol) was added and the mixture was stirred at room temperature under Ar for 1 h. The mixture was then evaporated and purification by chromatography (silica, 1 to 10% methanol in dichloromethane) afforded the title compound (36 mg, 57%) as a light yellow solid after recrystallisation from methanol-water. MS: m/e=369.2 [M+H]⁺.

Example 11

4-Methyl-2-[(E)-2-(3-methyl-5-pyridin-2-yl-3H-[1,2,3]triazol-4-yl)-vinyl]-thiazole-5-carboxylic acid (tetrahydro-pyran-4-yl)-amide

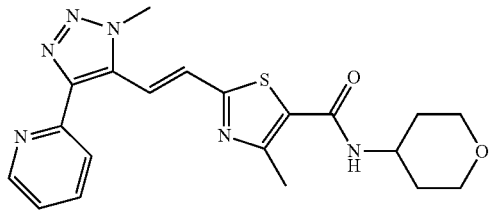 [SMILES: Cc1nc(/C=C/c2c(-c3ccccn3)nnn2C)sc1C(=O)NC1CCOCC1]

As described for example 10 g, 4-methyl-2-[(E)-2-(3-methyl-5-pyridin-2-yl-3H-[1,2,3]triazol-4-yl)-vinyl]-thiazole-5-carboxylic acid (56 mg, 0.17 mmol), was converted, using 4-aminotetrahydropyran instead of isopropylamine, to the title compound (46 mg, 66%) which was obtained as a light yellow solid. MS: m/e=411.2 [M+H]⁺.

Biochemical Assay

The ability of compounds present invention to bind to GABA A receptor subtypes was determined by competition for [³H]flumazenil (85 Ci/mmol; Roche) binding to HEK293 cells expressing rat (stably transfected) or human (transiently transfected) receptors of composition α1β2/3γ2, α2β3γ2, α3β3γ2 and α5β3γ2.

Membrane Preparation

Cell pellets were suspended in Krebs-tris buffer (4.8 mM KCl, 1.2 mM CaCl₂, 1.2 mM MgCl₂, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand Binding Assay

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of 10-10⁻³×10⁻⁶ M. Nonspecific binding was defined by 10⁻⁵ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting.

Data Calculation $K_i$ values were calculated using Excel-Fit (Microsoft) and are the means of two determinations. The compounds of the accompanying examples were tested in the above described assay, and the particular compounds were found to possess a $K_i$ value for displacement of [³H]flumazenil from α5 subunits of the rat GABA A receptor of 100 nM or less. A particular embodiment embraces compounds with a $K_i$ of 35 nM or less. In a particular embodiment the compounds of the invention are binding selectively for the α5 subunit relative to the α1, α2 and α3 subunit.

Representative test results, obtained by the above described assay measuring binding affinity to HEK293 cells expressing human (h) receptors, are shown in Table 1 below.

TABLE 1

Binding affinities to HEK293 cells expressing human (h) receptors of representative examples.

| Ex. | h$K_i$ GABA Aα5 [nM] |
|---|---|
| 1 | 28.8 |
| 2 | 45.3 |
| 3 | 15.7 |
| 4 | 22.2 |
| 5 | 43.2 |
| 6 | 11.3 |
| 7 | 6.2 |
| 8 | 2.6 |
| 9 | 6.8 |
| 10 | 20.7 |
| 11 | 12.7 |

The invention claimed is:
1. A compound of formula (I)

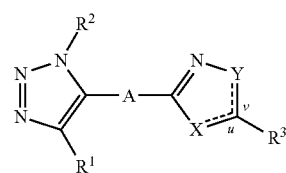

wherein
A —CH═CH—;
X is S or CH;
Y is O, NR⁹ or CR⁹, with the proviso that if X is S then Y is CR⁹ and if X is CH then Y is O or NR⁹;
u and v each independently represent a single bond or a double bond, with the proviso that u and v are not both double bonds and are not both single bonds;

R¹ and R² are each independently alkyl, aryl optionally substituted by 1 or 2 halo or heteroaryl optionally substituted by 1 or 2 halo, wherein one of R¹ and R² is alkyl;

R³ is halo, cyano, alkyl, haloalkyl, nitro, —C(O)R⁴, or —C(O)NR⁵R⁶;

R⁴ is H, alkyl, aryl, hydroxy, alkoxy or aryloxy;

R⁵ is H, alkyl, haloalkyl, hydroxyalkyl, —(CH₂)ₙ-cycloalkyl, —(CH₂)ₙ-heterocycloalkyl —(CH₂)ₙ-aryl, —(CH₂)ₙ-heteroaryl, —(CH₂)ₘ—NR⁷R⁸, or —(CH₂)ₘ—OR⁷, wherein cycloalkyl, heterocycloalkyl, aryl and heteroaryl are optionally substituted by halo, alkyl, haloalkyl, hydroxyalkyl, or alkoxy;

R⁶ is H, alkyl, or is alkylene together with R⁹;

or R⁵ and R⁶ together with the nitrogen to which they are bound form a heterocycloalkyl;

R⁷ and R⁸ are each independently H, alkyl, or aryl;

R⁹ is H, alkyl, or R⁹ is alkylene together with R⁶;

n is an integer from 0 to 6; and m is an integer from 2 to 6;

or a pharmaceutically acceptable salt thereof.

2. The compound of claim 1, wherein
A is —CH=CH—;
X is S or CH;
Y is O, NR⁹ or CR⁹, with the proviso that if X is S then Y is CR⁹ and if X is CH then Y is O or NR⁹;
u and v each independently represent a single bond or a double bond, with the proviso that u and v are not both double bonds and are not both single bonds;
R¹ and R² are each independently alkyl, aryl optionally substituted by one halo or heteroaryl, wherein one of R¹ and R² is alkyl;
R³ is —C(O)NR⁵R⁶;
R⁵ is alkyl, or heterocycloalkyl optionally substituted by alkyl;
R⁶ is H;
R⁹ is H or alkyl;
or a pharmaceutically acceptable salt thereof.

3. The compound of claim 1, wherein X is S and Y is CR⁹.

4. The compound of claim 3, wherein X is S, Y is CR⁹, u is a single bond and v is a double bond.

5. The compound of claim 1, wherein X is CH and Y is O.

6. The compound of claim 5, wherein X is CH, Y is O, u is a double bond and v is a single bond.

7. The compound of claim 1, wherein X is CH and Y is NR⁹.

8. The compound of claim 7, wherein X is CH, Y is NR⁹, u is a double bond and v is a single bond.

9. The compound of claim 1, wherein A is CH=CH.

10. The compound of claim 1, wherein X and Y together with the carbon and nitrogen atoms to which they are bound form a 5-membered heteroaryl.

11. The compound of claim 10, wherein the 5-membered heteroaryl is thiazol-2-yl, isoxazol-3-yl, or pyrazol-3-yl.

12. The compound of claim 1, wherein one of R¹ and R² is alkyl and the other is aryl optionally substituted by one halo or is heteroaryl optionally substituted by one halo.

13. The compound of claim 12, wherein one of R¹ and R² is methyl, ethyl, or butyl and the other is phenyl optionally substituted by one halo or pyridinyl optionally substituted by one halo.

14. The compound of claim 13, wherein one of R¹ and R² is methyl and the other is phenyl substituted by one fluoro or is pyridinyl.

15. The compound of claim 12, wherein R¹ is alkyl and R² is aryl or aryl substituted by one halo.

16. The compound of claim 15, wherein R¹ is methyl and R² is phenyl substituted by one fluoro.

17. The compound of claim 12, wherein R² is alkyl and R¹ is aryl, aryl substituted by one halo, heteroaryl, or heteroaryl substituted by one halo.

18. The compound of claim 17, wherein R² is methyl and R¹ is phenyl substituted by one fluoro or is pyridinyl.

19. The compound of claim 1, wherein R³ is —C(O)NR⁵R⁶.

20. The compound of claim 19, wherein R⁵ is alkyl or heterocycloalkyl optionally substituted by alkyl.

21. The compound of claim 20, wherein R⁵ is iso-propyl, oxetanyl substituted by methyl, tetrahydro-pyranyl, or morpholinyl.

22. The compound of claim 19, wherein R⁶ is H.

23. The compound of claim 1, wherein R⁹ is H or methyl.

24. The compound of claim 1, selected from the group consisting of:

3-[5-(4-Fluoro-phenyl)-3-methyl-3H-[1,2,3]triazol-4-ylmethoxy]-isoxazole-5-carboxylic acid (tetrahydro-pyran-4-yl)-amide;

5-[5-(4-Fluoro-phenyl)-3-methyl-3H-[1,2,3]triazol-4-ylmethoxy]-2-methyl-2H-pyrazole-3-carboxylic acid (tetrahydro-pyran-4-yl)-amide;

5-[3-(4-Fluoro-phenyl)-5-methyl-3H-[1,2,3]triazol-4-ylmethoxy]-2-methyl-2H-pyrazole-3-carboxylic acid (tetrahydro-pyran-4-yl)-amide;

5-[3-(4-Fluoro-phenyl)-5-methyl-3H-[1,2,3]triazol-4-ylmethoxy]-2-methyl-2H-pyrazole-3-carboxylic acid morpholin-4-ylamide;

5-[3-(4-Fluoro-phenyl)-5-methyl-3H-[1,2,3]triazol-4-ylmethoxy]-2-methyl-2H-pyrazole-3-carboxylic acid (3-methyl-oxetan-3-yl)-amide;

2-{(E)-2-[5-(4-Fluoro-phenyl)-3-methyl-3H-[1,2,3]triazol-4-yl]-vinyl}-4-methyl-thiazole-5-carboxylic acid isopropylamide;

2-{(E)-2-[5-(4-Fluoro-phenyl)-3-methyl-3H-[1,2,3]triazol-4-yl]-vinyl}-4-methyl-thiazole-5-carboxylic acid (tetrahydro-pyran-4-yl)-amide;

2-{(E)-2-[3-(4-Fluoro-phenyl)-5-methyl-3H-[1,2,3]triazol-4-yl]-vinyl}-4-methyl-thiazole-5-carboxylic acid (tetrahydro-pyran-4-yl)-amide;

2-{(E)-2-[3-(4-Fluoro-phenyl)-5-methyl-3H-[1,2,3]triazol-4-yl]-vinyl}-4-methyl-thiazole-5-carboxylic acid isopropylamide;

4-Methyl-2-[(E)-2-(3-methyl-5-pyridin-2-yl-3H-[1,2,3]triazol-4-yl)-vinyl]-thiazole-5-carboxylic acid isopropylamide; and 4-Methyl-2-[(E)-2-(3-methyl-5-pyridin-2-yl-3H-[1,2,3]triazol-4-yl)-vinyl]-thiazole-5-carboxylic acid (tetrahydro-pyran-4-yl)-amide;

or a pharmaceutically acceptable salt thereof.

25. The compound of claim 1, having formula (Ia)

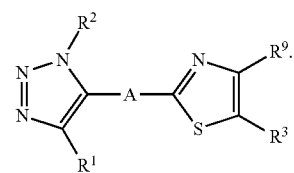

(Ia)

26. The compound of claim 1, having formula (Ib)

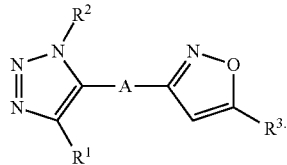
(Ib)

27. The compound of claim 1, having formula (Ic)

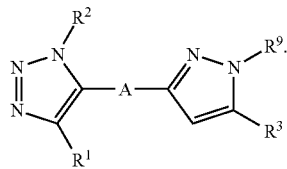
(Ic)

28. The compound of claim 1, having formula (I")

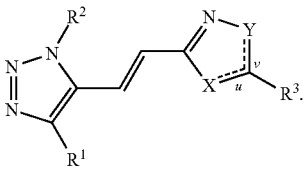
(I")

29. A pharmaceutical composition comprising a therapeutically effective amount of a compound of formula I

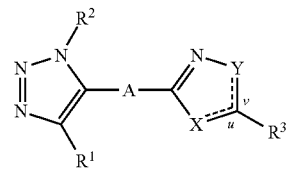
(I)

wherein
A is —CH=CH—;
X is S or CH;
Y is O, NR$^9$ or CR$^9$, with the proviso that if X is S then Y is CR$^9$ and if X is CH then Y is O or NR$^9$;
u and v each independently represent a single bond or a double bond, with the proviso that u and v are not both double bonds and are not both single bonds;
R$^1$ and R$^2$ are each independently alkyl, aryl optionally substituted by 1 or 2 halo or heteroaryl optionally substituted by 1 or 2 halo, wherein one of R$^1$ and R$^2$ is alkyl;
R$^3$ is halo, cyano, alkyl, haloalkyl, nitro, —C(O)R$^4$, or —C(O)NR$^5$R$^6$;
R$^4$ is H, alkyl, aryl, hydroxy, alkoxy or aryloxy;
R$^5$ is H, alkyl, haloalkyl, hydroxyalkyl, —(CH$_2$)$_n$-cycloalkyl, —(CH$_2$)$_n$-heterocycloalkyl —(CH$_2$)$_n$-aryl, —(CH$_2$)$_n$-heteroaryl, —(CH$_2$)$_m$—NR$^7$R$^8$, or —(CH$_2$)$_m$—OR$^7$, wherein cycloalkyl, heterocycloalkyl, aryl and heteroaryl are optionally substituted by halo, alkyl, haloalkyl, hydroxyalkyl, or alkoxy;
R$^6$ is H, alkyl, or is alkylene together with R$^9$;
or R$^5$ and R$^6$ together with the nitrogen to which they are bound form a heterocycloalkyl;
R$^7$ and R$^8$ are each independently H, alkyl, or aryl;
R$^9$ is H, alkyl, or R$^9$ is alkylene together with R$^6$;
n is an integer from 0 to 6; and
m is an integer from 2 to 6;
or a pharmaceutically acceptable salt thereof and a pharmaceutically acceptable carrier.

\* \* \* \* \*